United States Patent [19]

Thunberg

[11] Patent Number: 5,274,151
[45] Date of Patent: Dec. 28, 1993

[54] PROCESS FOR THE PREPARATION OF SOLID IRON (III) COMPLEXES

[75] Inventor: Jon C. Thunberg, Milford, N.H.

[73] Assignee: Hampshire Chemical Corp., Lexington, Mass.

[21] Appl. No.: 958,376

[22] Filed: Oct. 8, 1992

Related U.S. Application Data

[62] Division of Ser. No. 700,722, May 15, 1991, Pat. No. 5,159,094.

[51] Int. Cl.$^5$ ............................................. C07F 15/02
[52] U.S. Cl. ................................... 556/148; 423/138; 423/143; 423/179; 252/182.33; 252/182.34; 252/183.13; 71/DIG. 2
[58] Field of Search ................. 556/148; 423/138, 143, 423/179; 252/182.33, 182.34, 183.13; 71/DIG. 2

[56] References Cited

U.S. PATENT DOCUMENTS

| | | | |
|---|---|---|---|
| 2,816,060 | 12/1957 | Carter | 167/68 |
| 2,891,854 | 6/1959 | Kroll et al. | 71/1 |
| 4,056,381 | 11/1977 | Kenton | 71/36 |
| 4,130,582 | 12/1978 | Petree et al. | 562/448 |
| 4,181,516 | 1/1980 | Gray | 71/25 |

FOREIGN PATENT DOCUMENTS 0021690 2/1983 Japan ................................. 556/148

*Primary Examiner*—José G. Dees
*Assistant Examiner*—Porfirio Nazario
*Attorney, Agent, or Firm*—Nields & Lemack

[57] ABSTRACT

Fe(III) complexes having high bulk density and a process for the production of the same without the generation of heavy metal-contaminated effluents are disclosed. Solid complexes of EDTANaFe and EDTAKFe having high bulk densities are formed by reaction with ferric sulfate containing low chromium levels, followed by total drying of the resulting mixture in the same processing equipment without the prior separation of the sulfate salts formed.

3 Claims, No Drawings

PROCESS FOR THE PREPARATION OF SOLID IRON (III) COMPLEXES

This is a division of application Ser. No. 07/700,722, filed May 15, 1991, now U.S. Pat. No. 5,159,094.

BACKGROUND OF THE INVENTION

Conventional processes for the production of solid Fe(III) chelates for agricultural and other uses generate waste crystal liquors with high concentrations of iron and heavy metals, particularly chromium. Such heavy metals are problematic from an environmental standpoint. The economic implications of properly disposing of such streams are significant, and are often prohibitive. In addition, the waste liquor can contain some soluble Product. Although disposal of the waste liquors without recovering the product results in yield loss, recovery of contained product is not economical.

A conventional process for producing the complexes involves reacting chelating agents, such as EDTANa$_4$ or DTPANa$_5$, with ferric chloride solution, followed by filtration, washing and drying. However, one major source of chromium contamination is the ferric chloride used as the ferric iron source. Where low cost grade ferric chloride derived from scrap iron is used, the chromium concentration of the waste streams produced is on the order of 30 ppm. Higher grade ferric chloride can be used, which can reduce the chromium concentration in the waste streams to about 2–3 ppm; however, this higher grade ferric chloride is more expensive. A further drawback of ferric chloride is the highly corrosive properties of the slurries and liquors produced from the chelating agent/ferric chloride reactions.

Prior art drying processes include spray drying and drum drying. However, the resulting product is often very dusty, which creates handling problems jacketed vessel. Scrapers on the agitator shaft are instrumental in freeing the heat transfer surface of dried material. The equipment produces some agglomeration, which leads to the high bulk density of the product. In addition, high shear choppers reduce large agglomerate masses to promote thoroughly dried particle interiors. Preferably the equipment utilizes hydraulic drive. Such equipment is available from Littleford Bros., Inc., Florence, Ky.

Prior to drying, a slurry is formed by reaction of pH-adjusted chelating agents with an iron source, preferably 50% ferric sulfate solution. The reaction is illustrated for EDTANa$_4$ as follows:

$$EDTANa_4 + 0.5Fe_2(SO_4)_3 \longrightarrow EDTANaFe + 1.5Na_2SO_4.$$

Other salts of the chelating agents can be used, such as the potassium salts. The PH-adjusted chelating agent is prepared by neutralizing free alkali metal (e.g., sodium or potassium) hydroxide with the acid chelate, or with a mineral acid, such as 50% or 93% sulfuric acid. The chelating agent is available from W. R. Grace & Co.-Conn. as Hamp-Ene$^R$ 100S and is one of the feedstocks to the reactor/dryer. A slurry is then formed by reacting the chelating agent with ferric sulfate solution at about 40°–50° C. Preferably the chelating agent is as concentrated as possible in order to reduce the evaporative load on the drying equipment utilized. In the same piece of equipment, the resulting slurry is vacuum dried to a blend of the alkali metal salt of the iron (III) chelate and alkali metal sulfate. In contrast to conventional spray drying processes, the instant vacuum drying employs relatively long residence times which depend upon the steam pressure and the vacuum applied.

Since the entire product is vacuum dried without separation of the alkali metal sulfate salt formed, no effluent is produced and the yield is 100% (less any physical losses that occur). Although the iron content of the final product is lower than the prior art products from which the salt has been separated, a significant savings results from the absence of any effluent and the said 100% yield of product.

One surprising aspect of the instant process is the high bulk density of the resulting product formed. A comparison of the total iron content and bulk densitites of the products formed in accordance with the instant invention with that of the iron chelate formed from a prior art process (wherein the alkali metal chloride salt has been separated) is illustrated in Table 1.

TABLE 1

| PRODUCT | % Fe | BULK DENSITY LB/Cu Ft |
|---|---|---|
| EDTANaFe (prior art) | 12.6 | 37.1 |
| EDTANFe/Na$_2$SO$_4$ | 8.73 | 62.1 |
| EDTAKFe/K$_2$SO$_4$ | 7.80 | 61.8 |

The very high bulk densities of the instant products is a further advantage which offsets the slightly lower iron content of the products due to the presence of the alkali metal sulfate.

The total dried product may be milled to remove any gritty material. For commercial applications, it may be desirable to have 100% of the material pass through a 25 mesh sieve. A sieve analysis has demonstrated that about 7% of EDTANaFe/Na$_4$SO$_4$ is greater than 25 mesh and therefore requires milling to meet the desirable specifications.

It would be obvious to those silled in the art that the disclosed process should be generally applicable to preparation of the Fe(III) complexes of ligands other than EDTA.

The following examples will serve to illustrate various embodiments of the instant invention.

EXAMPLE 1

Production of DETANaFe/Na$_2$SO$_4$

The equipment used was a Littleford reactor/dryer MR5. EDTANa$_4$ solution was charged to a hold tank and free alkali therein was neutralized with 93% sulfuric acid. As the iron source, 50% Fe$_2$(SO$_4$)$_3$ was used. The Fe$_2$(SO$_4$)$_3$ was charged to the reactor/dryer and warmed to about 40° C. The neutralized chelate was then added in an amount of 3% excess over iron, and the resulting slurry was vacuumed dried to a blend of EDTANaFe and Na$_2$SO$_4$. The data are provided in Table II.

EXAMPLE 2

Production of EDTAKFe/K$_2$SO$_4$

The reaction and drying were carried out as in Example 1, except that the chelating agent was EDTAK$_4$ solution. The data are provided in Table III.

TABLE II

SCALE = 1.0 LB MOLE OF IRON

| | % Active Ingredient | Molecular Weight | Moles | Weight At 100% | Actual A.I. | Sp. Gravity | Lb/gal | Gallons |
|---|---|---|---|---|---|---|---|---|
| TO PRODUCE EDTANaFe - PRODUCT CODE NOS. 150 & 600 | | | | | | | | |
| HampEne 100 S (EDTANa4) | 38.0% | 380.2 | 1.030 | 392 | 1031 | 1.270 | 10.6 | 97.4 |
| Free NaOH in H-100 S | 1.5% | 40.0 | 0.386 | 15 | | | | |
| H2SO4 | 93.0% | 98.0 | 0.193 | 19 | 20 | 1.840 | 15.3 | 1.3 |
| Fe2(SO4)3 | 50.0% | 399.9 | 0.500 | 200 | 400 | 1.440 | 12.0 | 33.3 |
| Water | | | | | 0 | | | |
| Total PRODUCT | | | | | 1451 | | | 132.1 |
| EDTANaFe | | 367.1 | 1.000 | 367 | | | | |
| Na2SO4 | | 142.0 | 1.693 | 240 | | | | |
| Total Anhydrous Pure Product | | | | 608 | | | | |
| Total Product @ Fe Content of | 8.7% | | | 642 | | | | |

Note: the 8.7% Fe value was the Fe content of product produced from the Littleford trial

TABLE III

| | % Active Ingredient | Molecular Weight | Moles | Weight At 100% | Actual A.I. | Sp. Gravity | Lb/gal | Gallons |
|---|---|---|---|---|---|---|---|---|
| TO PRODUCE EDTAKFe | | | | | | | | |
| HampEne K4 100 S (EDTAK4) | 44.4% | 444.6 | 1.030 | 458 | 1031 | 1.320 | 11.0 | 93.8 |
| Free KOH in H-K4-100 S | 1.5% | 56.1 | 0.276 | 15 | | | | |
| H2SO4 | 93.0% | 98.0 | 0.138 | 14 | 15 | 1.840 | 15.3 | 0.9 |
| Fe2(SO4)3 | 50.0% | 399.9 | 0.500 | 200 | 400 | 1.440 | 12.0 | 33.3 |
| Water | | | | | 0 | | | |
| Total PRODUCT | | | | | 1446 | | | 128.1 |
| EDTAKFe | | 383.2 | 1.000 | 383 | | | | |
| K2SO4 | | 174.3 | 1.638 | 285 | | | | |
| Total Anhydrous Pure Product | | | | 669 | | | | |
| Total Product @ Fe Content of | 7.8% | | | 716 | | | | |

Note: the 7.8% Fe value was the Fe content of product produced from the Littleford trial

What is claimed is:

1. A dry solid composition consisting essentially of EDTANaFe.xH$_2$O and Na$_2$SO$_4$ having a bulk density of about 60 pounds per cubic foot.

2. A dry solid composition consisting essentially of EDTAKFe.xH$_2$O and K$_2$SO$_4$ having a bulk density of about 60 pounds per cubic foot.

3. Iron (III) complexes of alkali metal salts of EDTA, produced by a process comprising:

a. Neutralizing free alkali present in an alkali metal salt solution of EDTA with acid;

b. Reacting the neutralized alkali metal salt solution with ferric sulfate to form a slurry containing alkali metal sulfate;

c. Vacuum drying said slurry without the prior separation of said alkali metal sulfate, said reacting and vacuum drying steps being carried out in the same processing equipment.

* * * * *

UNITED STATES PATENT AND TRADEMARK OFFICE
CERTIFICATE OF CORRECTION

PATENT NO. : 5,274,151
DATED : December 28, 1993
INVENTOR(S) : Jon C. Thunberg

It is certified that error appears in the above-indentified patent and that said Letters Patent is hereby corrected as shown below:

Column 1, Line 38, insert a period after "handling problems"

Signed and Sealed this

Seventeenth Day of January, 1995

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO. : 5,274,151

DATED : December 28, 1993

INVENTOR(S) : Jon C. Thunberg

It is certified that error appears in the above-indentified patent and that said Letters Patent is hereby corrected as shown below:

Column 1, line 38, before "jacketed" insert the following:
--Accordingly, there is a need to find an alternative production process which reduces or eliminates the generation of high heavy metal effluents without adding significant cost.

SUMMARY OF THE INVENTION

--The problems of the prior art have been solved by the instant invention, which provides solid Fe(III) complexes having high bulk density and a process for the production of the same without the generation of heavy metal-contaminated effluents. In particular, the present invention relates to the production of solid complexes of EDTANaFe and EDTAKFe having high bulk densities by reaction with ferric sulfate containing low chronium levels, followed by total drying of the resulting mixture without the prior separation of the sulfate salts formed. The reaction and drying process are carried out in the same processing equipment. By eliminating the separation step and drying the total reaction product, no waste liquor is generated.

UNITED STATES PATENT AND TRADEMARK OFFICE
CERTIFICATE OF CORRECTION

PATENT NO. : 5,274,151
DATED : December 28, 1993
INVENTOR(S) : Jon C. Thunberg

It is certified that error appears in the above-indentified patent and that said Letters Patent is hereby corrected as shown below:

The product loss of prior art processes due to the presence of some soluble product in the waste liquor is thereby eliminated.

DETAILED DESCRIPTION OF THE INVENTION

—The present invention concerns a total drying process for iron(III) complexes, and the resulting products formed thereby. Preferably the equipment used is a high torque combination of a mixer with a reactor dryer, such that the mixing or reaction and the drying are carried out in the same equipment chamber. The equipment should be constructed of stainless steel, preferably 316 stainless steel. Suitable equipment utilizes a mechanically fluidized ploughshare action to agitate the particles to be dried. This action forces particle surfaces to be continually exposed to the heated interior walls of the—

Signed and Sealed this

Thirtieth Day of May, 1995

*Attest:*

BRUCE LEHMAN

*Attesting Officer*   Commissioner of Patents and Trademarks